United States Patent [19]
Henkin et al.

[11] Patent Number: 5,507,280
[45] Date of Patent: Apr. 16, 1996

[54] ANESTHESIA REBREATHING SYSTEM

[76] Inventors: Melvyn L. Henkin, 1001 Sharon La.; Jordan M. Laby, 1389 Beachmont, both of, Ventura, Calif. 93001

[21] Appl. No.: 405,582

[22] Filed: Mar. 17, 1995

Related U.S. Application Data

[63] Continuation-in-part of Ser. No. 960,935, Oct. 14, 1992, Pat. No. 5,398,675.

[51] Int. Cl.$^6$ .................................................. A61M 15/00
[52] U.S. Cl. .................. 128/203.12; 128/203.28; 128/205.15
[58] Field of Search .......... 128/203.12, 205.13, 128/205.14, 205.15, 205.17, 203.28

[56] References Cited

U.S. PATENT DOCUMENTS

| | | | |
|---|---|---|---|
| 3,292,617 | 12/1966 | McDonough | 128/205.15 |
| 3,831,595 | 8/1974 | Valenta et al. | 128/205.15 |
| 3,841,327 | 10/1974 | Hay | 128/205.17 |
| 4,811,732 | 3/1989 | Harung | 128/205.17 |
| 4,991,576 | 2/1991 | Henkin et al. | 128/203.28 |
| 5,398,675 | 3/1995 | Henkin et al. | 128/203.12 |

FOREIGN PATENT DOCUMENTS

| | | | |
|---|---|---|---|
| 685702 | 5/1964 | Canada | 128/205.15 |
| 1238411 | 7/1971 | United Kingdom | 128/205.15 |

*Primary Examiner*—Aaron J. Lewis
*Attorney, Agent, or Firm*—Freilich Hornbaker Rosen

[57] ABSTRACT

A system for administering anesthesia gas and for preventing gas overflow until the patient breathing reservoir is full in order to enhance ease of use, safety, and efficient utilization of anesthesia gas. Overflow from a patient Pop-Off valve is inhibited by an Overflow Blocker valve mounted downstream in series opposition to the patient Pop-Off valve. The Overflow Blocker valve is forced open when the patient bag is full. Thus, until the patient bag is full, the loss of patient exhaled dead space gas and fresh gas is prevented.

12 Claims, 4 Drawing Sheets

ANESTHESIA REBREATHING SYSTEM

RELATED APPLICATIONS

This is a continuation-in-part of U.S. patent application Ser. No. 07/960,935, filed Oct. 14, 1992, now U.S. Pat. No. 5,398,675, which is incorporated herein by reference.

FIELD OF THE INVENTION

This invention relates generally to systems for administering anesthesia gas to medical patients.

BACKGROUND OF THE INVENTION

U.S. Pat. Nos. 3,814,091 and 3,901,230 disclose anesthesia rebreathing systems characterized by a geometry which preferentially vents expired alveolar gas, rich in carbon dioxide ($CO_2$), while retaining fresh gas and initially expired dead space gas, rich in oxygen ($O_2$), for rebreathing by the patient to thus minimize the need for $CO_2$ absorption. The systems include a patient circuit incorporating an overflow tube whose entrance is located very close to the patient. The overflow tube exits at a patient overflow (commonly referred to as "Pop-Off") valve which is located close to an anesthesia machine where it can be conveniently controlled by an attending anesthetist. By locating the overflow tube entrance close to the patient, it functions to preferentially vent alveolar gas through the patient overflow (i.e., Pop-Off) valve and save dead space and unbreathed gas within the tubing and reservoir of the patient circuit. The Pop-Off valve is operable in two different modes, i.e., (1) as a manually controlled variable orifice for spontaneous, manually assisted or controlled ventilation and (2) as an automatically controlled valve responding to a positive control pressure for manually assisted or controlled ventilation or mechanically controlled ventilation.

The enhanced system described in U.S. Pat. No. 3,901,230 can be viewed as functionally including (1) a patient circuit and (2) a ventilator/isolator (V/I) circuit for controlling gas volume and pressure in the patient circuit. The described structural embodiment can be viewed as physically including (1) a single use portion and (2) a reusable portion. The embodiment is configured so that the single use portion forms most of the patient circuit with the reusable portion forming the V/I circuit and part of the patient circuit, e.g. the patient Pop-Off Valve. The V/I circuit includes a constant volume (e.g., rigid) container (forming part of the system's reusable portion) within which a variable volume patient breathing reservoir (e.g., a flaccid bag) (forming part of the single use portion) is accommodated. The pressure within the rigid container is controlled (1) during manually assisted or controlled ventilation, by an attending anesthetist squeezing an outside bag and (2) during mechanically controlled ventilation by a conventional ventilator. The pressure variations in the rigid container are applied to the patient circuit via the flexible walls of the patient bag. Cross contamination is eliminated because the patient expired gas cannot come into contact with the reusable portion components exposed to inspired gas.

U.S. Pat. No. 4,991,576 discloses an anesthesia rebreathing system which retains the advantages of the systems disclosed in U.S. Pat. Nos. 3,814,091 and 3,901,230 and which incorporates additional features to enhance ease of use and safe operation. It describes first and second embodiments which differ from one another in that the first embodiment uses overflow gas from the patient circuit as working gas for the V/I circuit whereas the second embodiment derives V/I working gas from a high pressure gas source (preferably dry medical grade oxygen).

Applicants' parent application discloses improvements particularly suited for use in systems of the type described in U.S. Pat. No. 4,991,576, for enhancing ease of use, safe operation, and efficient use of anesthesia gas. More particularly, the improvements include a control subsystem for maintaining the patient overflow (i.e., Pop-Off) valve closed during each breathing cycle until the patient breathing reservoir is full. As a consequence, loss of patient exhaled dead space gas and fresh gas is minimized. In the preferred embodiment described, the patient reservoir comprises a flaccid bag and the control subsystem includes a "full bag" sensor which, via a pneumatic cylinder, physically holds the patient Pop-Off valve closed except when the bag is full. The full-bag sensor preferably comprises a lever mounted adjacent to the patient breathing bag and biased to a first position. As the volume of the bag increases, its wall engages the lever to move it from its first position to a second or full-bag position. The lever, in turn, releases the aforementioned pneumatic cylinder to allow the Pop-Off valve to open.

SUMMARY OF THE INVENTION

The present invention is directed to an improved anesthesia rebreathing system configured for preventing gas overflow from a patient Pop-Off valve until the patient breathing reservoir is full, resulting in enhanced ease of use, safety, and efficient utilization of anesthesia gas.

In accordance with the invention, overflow from a patient Pop-Off valve is inhibited by an Overflow Blocker valve mounted downstream in series opposition to the patient Pop-Off valve. The Overflow Blocker valve is, however, forced open when the patient breathing reservoir, typically a flaccid bag, is full. Thus, until the patient bag is full, the loss of patient exhaled dead space gas and fresh gas is prevented.

The patient Pop-Off valve in preferred embodiments of the invention comprises a unidirectional valve configured to permit gas flow only in a first direction from its entrance port to its exit port, i.e., out of the patient circuit. The series opposing Overflow Blocker valve is configured so that it normally closes in response to gas flow in said first direction. However, a mechanical member responding to the volume of the patient bag filling to a predetermined volume physically opens the Overflow Blocker valve to allow patient overflow gas to flow therepast.

In a first preferred embodiment, the patient overflow gas is used as the working gas for a ventilator/isolator (V/I) circuit. In this embodiment, the Overflow Blocker valve is located between the patient Pop-Off valve and the working gas entrance to a fixed volume container accommodating the patient bag. Gas can flow into the container from the patient Pop-Off valve only when the patient bag is full and the Overflow Blocker valve is thus open. Excess gas from the container is vented through an adjustable V/I circuit Pop-Off valve to a scavenging system.

In a second preferred embodiment, V/I circuit working gas is derived from a high pressure gas source (preferably dry medical grade oxygen) rather than from the patient Pop-Off valve. This second embodiment is similar to the first embodiment to the extent that patient overflow gas flow past the patient Pop-Off valve occurs only when the Overflow Blocker valve is open as a consequence of the patient bag being full. However, this second embodiment differs from the first embodiment in that gas flow past the Overflow Blocker valve flows to a scavenging system rather than into the patient bag container.

DETAILED DESCRIPTION OF THE FIGURES

Inasmuch as preferred embodiments of the present invention are similar in many respects to the embodiments disclosed in Applicants' prior U.S. Pat. No. 5,398,675 the description herein will focus primarily on the features which distinguish the present invention. Although these features will be described with reference to systems of the type described in said U.S. Pat. No. 5,398,675 it is pointed out they are also applicable to many other anesthesia gas delivery systems.

Figure 1:
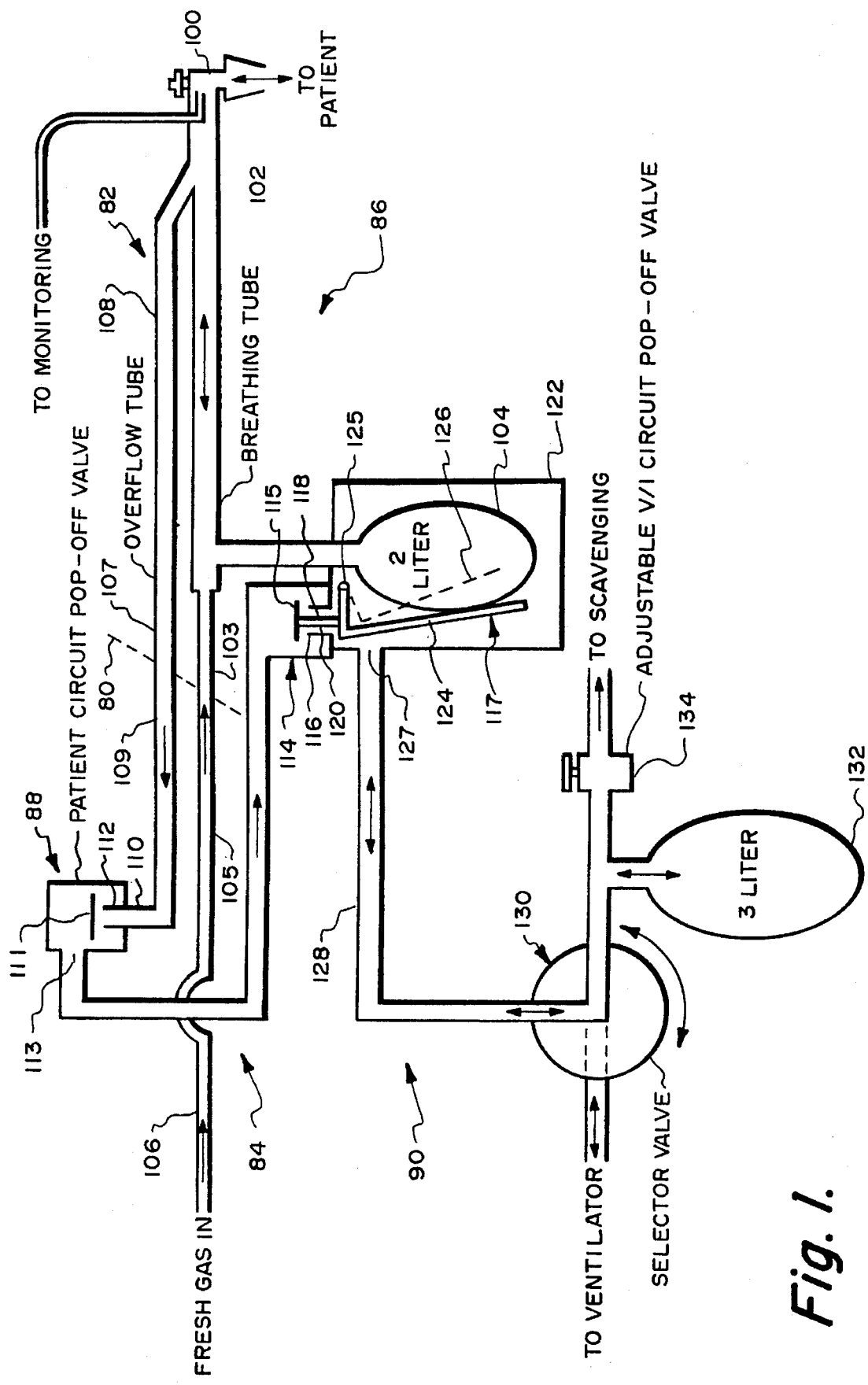
FIG. 1 is a functional block diagram of a first operational embodiment in accordance with the invention.

Attention is now directed to FIG. 1 which is a block diagram of a first preferred embodiment in accordance with the present invention. As in applicants parent application, the dashed line 80 is intended to generally represent a physical interface between a detachable single use structural portion 82 and a permanent reusable structural portion 84. The detachable portion 82 includes most of the components forming a functional patient circuit 86. However, a patient Pop-Off valve 88 may be properly viewed as functionally being part of the patient circuit 86 although it is physically included in the system's permanent portion 84. The permanent portion 84 primarily comprises a ventilator/isolator (V/I) circuit or subsystem 90 for controlling the gas volume and pressure in the patient circuit 86.

The patient circuit portion 86 is comprised of a device for communicating with a patient's airway, e.g., an elbow fitting 100 adapted to be coupled to a patient mask or endotracheal tube. The fitting 100 communicates with a breathing tube 102 which is shown as including a single limb for both expiratory and inspiratory gas movement but which can comprise separate inspiratory and expiratory tubes. The distal end of the breathing tube 102 is connected to the elbow fitting 100. The proximal end of the breathing tube 102 defines a fresh gas interface port 103 which is connected across the interface 80 to a fresh gas interface port 105 on the permanent portion 84. A variable volume patient breathing reservoir, e.g., flaccid bag 104 communicates with breathing tube 102 close to the interface port 103. The permanent portion fresh gas interface port 105 is coupled to a fresh gas supply line 106. The patient circuit portion 82 additionally includes an overflow tube 108 having a tube entrance located close to the patient, i.e. fitting 100. The proximal end of the overflow tube 108 at interface port 107 is connected to an interface port 109 across the interface 80. Interface port 109 opens to entrance port 110 of the Pop-Off valve 88.

The Pop-Off valve 88 preferably comprises a check valve element 111 slightly biased closed against a valve seat 112. The check valve element 111 is configured to permit gas flow therepast in a first direction only, i.e., into entrance port 110 and out from exit port 113 to Overflow Blocker valve 114.

Figure 3:
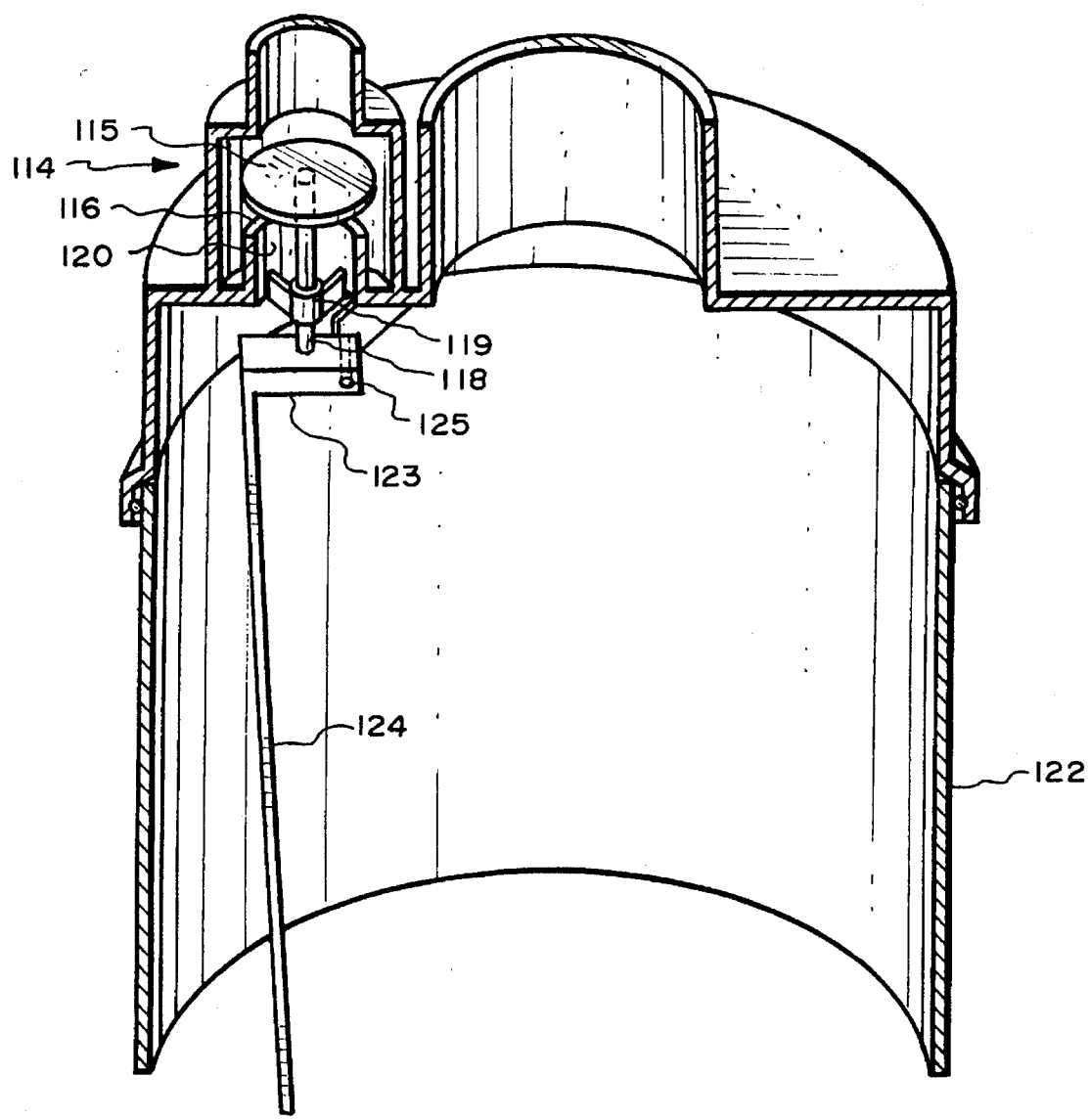
FIG. 3 depicts an implementation of a preferred Overflow Blocker Valve useful in the embodiment of FIG. 1.

As shown in FIGS. 1 and 3 Overflow Blocker valve 114 includes check valve element 115 and valve seat 116 and is configured in series opposition to Pop-Off valve 88 so that it normally closes in response to gas flow out of Pop-Off valve exit port 113. Accordingly, the series opposed Pop-Off and Overflow Blocker valves normally prevent any outflow from overflow tube 108 past Pop-Off valve 88. However, Overflow Blocker valve check valve element 115 is configured to be physically opened by lever 117 acting on lifter stem 118 when patient bag 104 is full. Lifter stem 118 is mounted in guide 119 for reciprocal vertical movement.

Note in FIG. 1 that Overflow Blocker valve 114 is located between Pop-Off valve exit port 113 and the entrance port 120 to a constant volume, e.g., rigid, container 122 in which the patient bag 104 is removably accommodated. The lever 117, comprised of short section 123 and long section 124, is mounted in container 122 for pivoting around pivot pin 125. When the volume of patient bag 104 is less than a predetermined threshold, lever 117 will pivot clockwise to the dashed line position 126. In this position, the Overflow Blocker valve element 115 is seated on valve seat 116 and outflow through Pop-Off valve exit port 113 is prevented.

On the other hand, when patient bag 104 fills beyond a predetermined threshold volume, the bag wall contacts lever long section 124 to pivot lever 117 clockwise to the full line position depicted in FIG. 1. This causes the lever short section 123 to lift lifter stem 118 and unseat valve element 115 to thus permit gas to flow out of exit port 113 and into container 122 via entrance port 120.

Changes in pressure within the container 122 are transferred to the patient circuit 86 via the flexible walls of the patient bag 104. Increases or decreases in gas volume within the patient bag are reflected by gas movement out of or into the rigid container 122 via control port 127 coupled via tube 128 to a mode selector valve 130.

Mode selector valve 130 can be selectively rotated by a user to either the full line position or the dashed line position depicted in FIG. 1. When in the full line position, valve 130 couples control port 127 to outside bag 132 and to a user adjustable V/I circuit Pop-Off valve 134. When in the dashed line position, valve 130 couples control port 127 to a mechanical ventilator (not shown).

In the operation of the system of FIG. 1, the selector valve 130 will be placed in the solid line position for manually assisted and controlled ventilation or spontaneous ventilation. In spontaneous ventilation, fresh gas will continually be supplied via supply line 106 to the patient bag 104 and breathing tube 102. As the patient starts to inhale, he generates a negative pressure which holds the patient circuit Pop-Off valve 88 closed. The patient bag 104 decreases in size as gas flows to the patient. The outside bag 132 also decreases in size as gas flows therefrom to the patient bag container 122. Under these conditions, the Overflow Blocker valve 114 is closed. At the start of expiration, gas flows from the patient and the fresh gas supply to the patient bag 104. As the patient bag fills, gas is displaced from the container 122 to the outside bag 132. When the outside bag 132 is full, the adjustable V/I circuit Pop-Off valve 134 will vent excess gas to a scavenging system via port 136.

At some point during expiration, including the end expiratory phase, the patient bag 104 becomes sufficiently full to pivot lever 117 to its full line position and thus open the Overflow Blocker valve 114. Consequently, gas from the patient flows through the overflow tube 108 and past the patient circuit Pop-Off valve 88 and Overflow Blocker valve 114 into the container 122. Excess gas is vented through valve 134.

When the Overflow Blocker valve 114 is open, the gas expired by the patient flows almost directly into the overflow tube 108. Simultaneously, the fresh gas inflow via supply line 106 pushes previously exhaled gas in the breathing tube 102, into the overflow tube 108. Consequently, the alveolar gas, that is last gas out of the patient, is the gas first into the overflow tube 108 for priority venting. At the conclusion of exhalation, both the patient bag 104 and the outside bag 132 are full and the inhalation sequence begins again.

The system operates similarly during manually assisted and controlled ventilation except that typically the V/I circuit Pop-Off valve 134 is incrementally adjusted by the attending anesthetist so that a proper volume of gas is vented to scavenging. During inspiration, the anesthetist squeezes the outside bag 132 sending gas with a positive pressure to the container 122 where it presses on the patient bag 104 which in turn sends gas to the patient via the breathing tube 102. Additionally, the pressure in the container 122 opens the Overflow Blocker valve 114 and closes the patient circuit Pop-Off valve 88. Just as during spontaneous ventilation, gas flows into the patient from the patient bag 104 and the fresh gas supply 106 during inspiration. Expiration and the end expiratory phase during manually assisted and controlled ventilation are essentially the same as during spontaneous ventilation.

When the selector valve 130 is in the dashed line position, control port 127 is coupled to a mechanical ventilator (not shown). In this mode, the mechanical ventilator acts essentially the same as the outside bag 132 being squeezed by the attending anesthetist.

Figure 2:
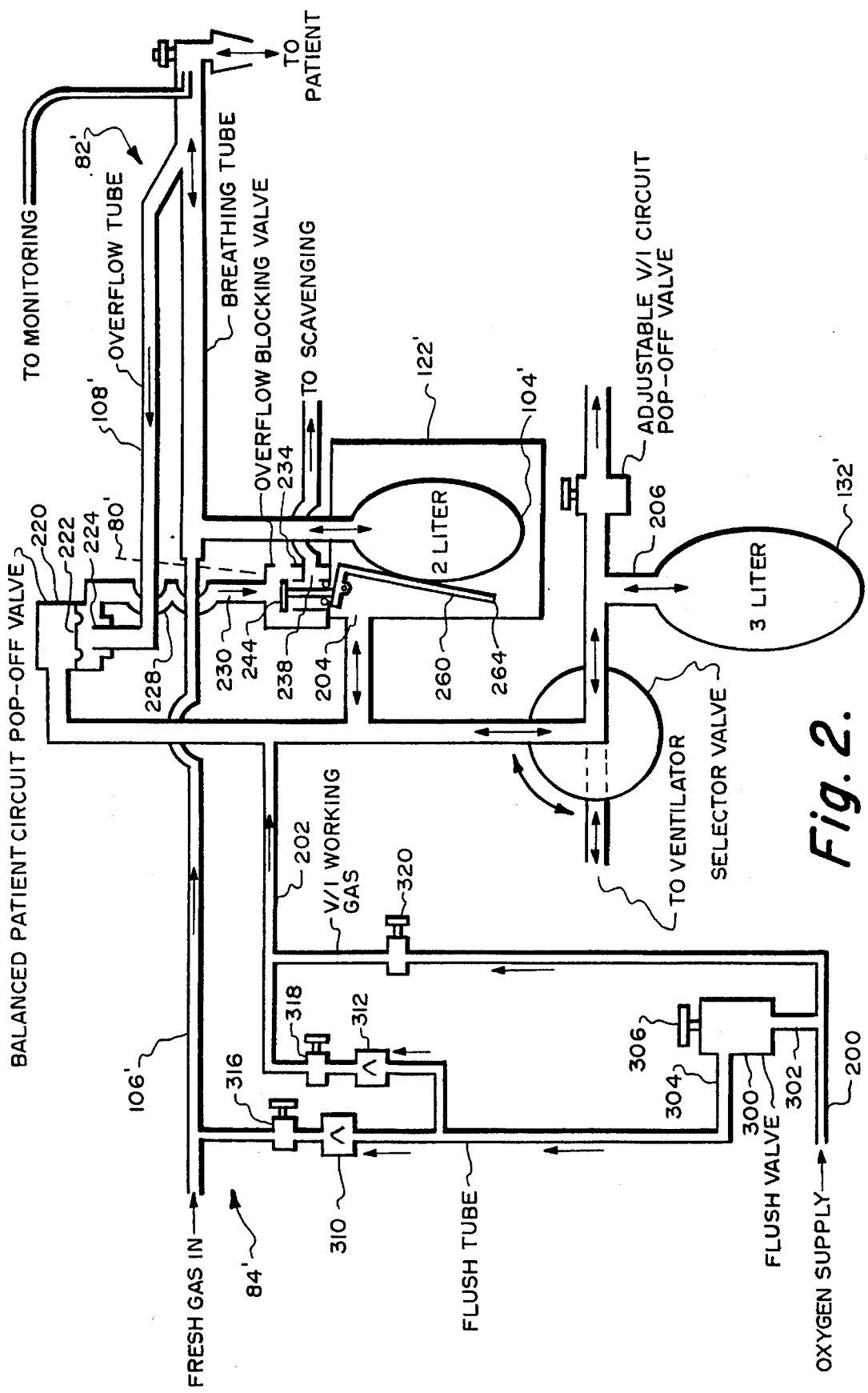
FIG. 2 is a functional block diagram of a second operational embodiment in accordance with the invention.

Attention is now directed to FIG. 2 which comprises a block diagram of a second preferred embodiment in accordance with the present invention. The detachable portion 82' of FIG. 2 can be identical to that shown in FIG. 1 and similarly communicates across interface 80' with a permanent portion 84'. The permanent portion 84' differs from the permanent portion 84 of FIG. 1 primarily as a consequence of using supplemental gas, e.g., dry medical grade oxygen, supplied via inlet tube 200, as V/I circuit working gas to fill, via tube 202, rigid container 122' (via port 204) and outside bag 132' (via port 206). The use of patient circuit gas as V/I circuit working gas in FIG. 1 does not present a cross contamination risk inasmuch as gas from the overflow tube 108 can only flow away from the patient past the Patient Pop-Off valve 88 and there is no path for the V/I circuit working gas to reenter the patient circuit. However, the disadvantage of using patient expired gas for V/I circuit working gas is that it is generally of high humidity and may have impurities, such as blood or phlegm which could, over extended periods, affect the reliability of valving and flow in the V/I circuit as well as the mechanical ventilator. Although this risk is minimal if the permanent portion is properly maintained, the system of FIG. 2 avoids this possibility by using a high pressure gas supply to provide working gas.

Figures 4A, 4B:
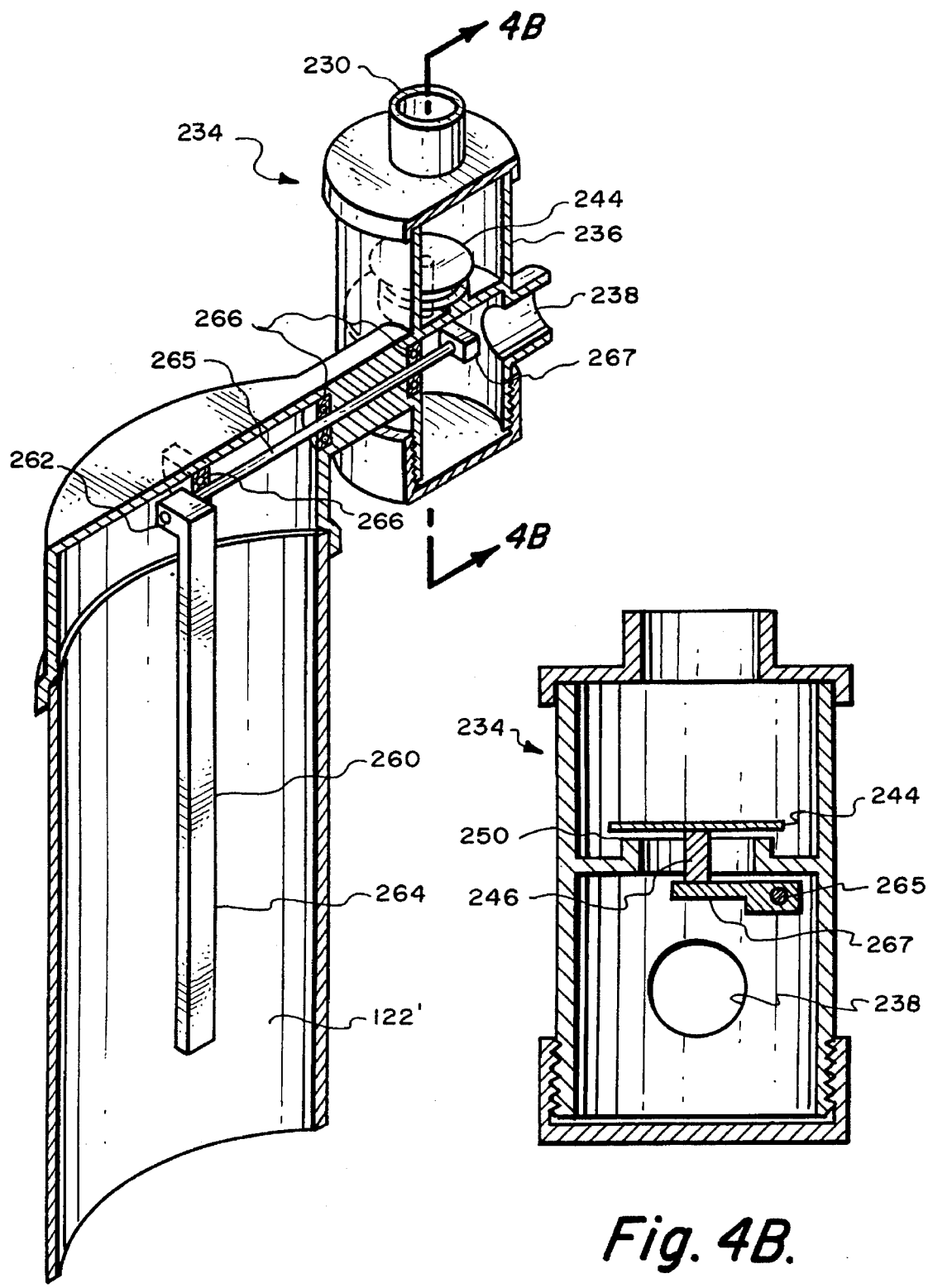
FIG. 4A depicts an implementation of a preferred Overflow Blocker Valve useful in the embodiment of FIG. 2.
FIG. 4B is a sectional view taken substantially along the plane 4B—4B of FIG. 4A.

Thus, it will be noted that the system of FIG. 2 differs from that of FIG. 1 in that instead of using a check valve as the Patient Pop-Off Valve 88, FIG. 2 uses a balanced valve 220 for this purpose. Valve 220 includes a diaphragm or valve element 222 which is normally slightly biased closed, i.e., in contact against valve seat 224. A sufficient positive pressure from overflow tube 108' can overcome this bias pressure to open valve 220 to permit gas flow from tube 108' past valve seat 224 and through tube 228 to port 230 of Overflow Blocker valve 234. As seen in FIGS. 4A and 4B, valve 234 is comprised of valve housing 236 which, in addition to port 230, defines port 238 which leads to a scavenging system (not shown). A valve element 244 is mounted in housing 236 on lifter stem 246 for reciprocal movement toward and away from valve seat 250. When valve 234 is closed, i.e., with valve element 244 engaging valve seat 250, gas flow out of the overflow tube 108' is prevented because the Pop-Off valve 220 and Overflow Blocker valve 234 are in series opposition.

Valve 234 is opened by the action of lever 260 acting on lifter stem 246 when patient bag 104' is full. Note that lever 260 is comprised of short and long sections 262, 264 and is mounted in container 122' for pivotal movement. More particularly, short section 262 has a rod 265 secured thereto extending through bearings 266. Rod 265 has a short arm 267 secured thereto in housing 236 for engaging lifter stem 246. In its normal state, the lever 260 will hang in a position which permits lifter stem 246 to drop so as to enable valve element 244 to seal against valve seat 250. As bag 104' fills beyond a predetermined volume, its wall engages lever 260 to pivot it clockwise (as viewed in FIG. 2) to lift lifter stem 246 (via rod 265 and arm 267) and open valve 234, enabling gas to flow from tube 108' past Patient Pop-Off valve 220 and via Overflow Blocker valve port 238 to scavenging.

FIG. 2 further differs from FIG. 1 in that a flush valve 300 is provided. The valve 300 includes an inlet port 302 and outlet port 304. An attending anesthetist can operate flush button 306 to flush gas from supply 200 to clear both the patient and V/I circuits.

Operation of the system of FIG. 2 is similar to that described for FIG. 1 except it should be noted that when the flush button 306 is pressed, with the Selector Valve 130' in the outside bag position, not only will high pressure gas be supplied to the fresh gas line 106' via check valve 310, for flushing the patient circuit, but in addition high pressure gas will be supplied via check valve 312 to the V/I circuit including rigid container 122' and outside bag 132' to properly fill both circuits. Needle valves 316, 318 are preferably incorporated in the system of FIG. 2, as shown, for optimizing the flows to the patient and V/I circuits. Additionally, an adjustable needle valve 320 is provided to enable the user to adjust the flow of V/I working gas.

From the foregoing, it should now be appreciated that improvements in anesthesia gas delivery systems have been disclosed herein primarily for enhancing safe operation and increasing the efficiency of anesthesia gas usage. Although preferred implementations have been described, it should be understood that various alternatives can be readily used without departing from the spirit of the invention or the intended scope of the appended claims. For example only, although both described embodiments show the Overflow Blocker valve downstream from the Patient Pop-Off valve, this order could be reversed if desired.

We claim:

1. An anesthesia gas rebreathing system including:

a patient airway communication device;

a breathing tube having a first port coupled to said patient airway communication device and a second port configured for coupling to a fresh gas supply;

a variable volume patient reservoir having an entrance opening coupled to said breathing tube proximate to said breathing tube second port;

a patient overflow valve having an entrance port coupled to said breathing tube proximate to said first port and configured to permit gas flow from said entrance port to an exit port thereof in response to a positive pressure thereacross;

an overflow blocker valve having a first port and a second port, and configured to close in response to a positive pressure from said first port to said second port for preventing gas flow therethrough;

said patient overflow valve exit port coupled to said overflow blocker valve first port; and sensor means responsive to said patient reservoir filling to a predetermined volume for holding said overflow blocker valve open to permit gas flow from said first to said second port thereof.

2. The system of claim 1 further including:

a constant volume container;

means in communication with said container for varying the pressure therein; and means mounting said variable volume patient reservoir in said container whereby pressure variations therein will produce corresponding variations in said reservoir.

3. The system of claim 2 wherein said container defines a pressure control port; and means coupled to said pressure control port for producing pressure variations in said container.

4. The system of claim 3 wherein said container defines a working gas entrance port and said overflow blocker valve second port is coupled to said container working gas entrance port.

5. The system of claim 3 wherein said overflow blocker valve second port is coupled to a scavenging system.

6. The system of claim 3 including a gas supply source coupled to said container entrance port for supplying working gas thereto.

7. The system of claim 3 wherein said means for producing pressure variations includes a gas container whose gas storage volume can be selectively varied by an operator.

8. The system of claim 1 wherein said patient reservoir includes an outer wall; and wherein said sensor means is responsive to the location of said reservoir outer wall.

9. The system of claim 8 wherein said sensor means includes a mechanical member mounted for movement from a first to a second position in response to said patient reservoir filling to a predetermined volume; and means coupling said mechanical member to said overflow blocker valve for holding said overflow blocker valve open when mechanical member is in said second position.

10. In a system for administering anesthesia gas to a patient including a breathing tube for supplying fresh gas to a patient's airway and a variable volume reservoir for alternately (1) storing gas from the patient during exhalation and (2) supplying stored gas to the patient during inhalation, means for controlling gas venting from said breathing tube, said means comprising:

a first valve coupled to said breathing tube for permitting gas flow therethrough in a first direction out of said breathing tube;

a second valve coupled in series with said first valve configured to normally prevent gas flow therethrough in said first direction; and sensor means responsive to said reservoir filling to a predetermined volume for holding said second valve open to permit gas flow therethrough in said first direction.

11. The system of claim 10 wherein said reservoir includes an outer wall; an wherein said sensor means is responsive to the location of said reservoir outer wall.

12. The system of claim 11 wherein said sensor means includes a mechanical member mounted for movement from a first to a second position in response to said patient reservoir filling to a predetermined volume; and means coupling said mechanical member to said overflow blocker valve for holding said overflow blocker valve open when mechanical member is in said second position.

* * * * *